US008067594B2

(12) United States Patent
Ahman et al.

(10) Patent No.: US 8,067,594 B2
(45) Date of Patent: Nov. 29, 2011

(54) PROCESS FOR THE PRODUCTION OF BENZOPYRAN-2-OL DERIVATIVES

(75) Inventors: Jens Bertil Ahman, Sandwich (GB);
Barry Richard Dillon, Sandwich (GB);
Alan John Pettman, Sandwich (GB)

(73) Assignee: Pfizer Inc., New York, NY (US)

( * ) Notice: Subject to any disclaimer, the term of this patent is extended or adjusted under 35 U.S.C. 154(b) by 274 days.

(21) Appl. No.: 12/302,228

(22) PCT Filed: May 21, 2007

(86) PCT No.: PCT/IB2007/001379
§ 371 (c)(1),
(2), (4) Date: Nov. 24, 2008

(87) PCT Pub. No.: WO2007/138440
PCT Pub. Date: Dec. 6, 2007

(65) Prior Publication Data
US 2009/0306384 A1    Dec. 10, 2009

Related U.S. Application Data

(60) Provisional application No. 60/803,068, filed on May 24, 2006.

(51) Int. Cl.
*C07D 311/20* (2006.01)
*C07D 311/58* (2006.01)
*C07C 215/54* (2006.01)
*C07C 213/02* (2006.01)
*C07C 219/28* (2006.01)

(52) U.S. Cl. ......... 544/376; 549/399; 560/140; 564/316
(58) Field of Classification Search .................. None
See application file for complete search history.

(56) References Cited

U.S. PATENT DOCUMENTS

| 5,733,936 A | 3/1998 | Buschmann et al. ......... 514/646 |
| 6,858,650 B1 | 2/2005 | Meese ............................ 514/530 |
| 2004/0209916 A1 | 10/2004 | Richards | |

FOREIGN PATENT DOCUMENTS

| EP | 1254890 | 11/2002 |
| WO | WO 9829402 | 7/1998 |
| WO | 9958478 | 11/1999 |
| WO | 0149649 | 7/2001 |

OTHER PUBLICATIONS

Jurd, L. "Synthesis of 4-phenyl-2H-1-benzopyrans", Journal of Heterocyclic Chemistry, vol. 28, No. 4, 1991, pp. 983-986.
Botteghi, C. et al., "A new efficient route to tolterodine", Organic Process Research & Development, vol. 6, No. 4, Jul. 2002, pp. 379-383.
Saimoto, et al., "Synthesis of 3,4-Dihydro-2H-Benzopyrans from Phenols and α,β-Unsaturated Carbonyl Compounds", Heterocycles, vol. 55, 2001, pp. 2051-2054.

*Primary Examiner* — Emily Bernhardt
(74) *Attorney, Agent, or Firm* — Jennifer A. Kispert; Richard V. Zanzalari

(57) ABSTRACT

The invention provides a process for producing a compound of formula (I),

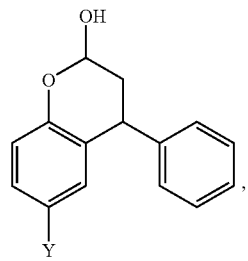

(I)

wherein Y is selected from the group consisting of $CH_3$, $CH_2OH$, $CH_2CH_2OH$, $CH_2Br$ and $Br$; comprising the steps of:
(i) reacting a compound of formula (II),

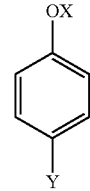

(II)

wherein OX represents hydroxy or $O^-M^+$, in which $M^+$ is a cation selected from $Li^+$, $Na^+$ and $K^+$, and
Y is as defined above;
with trans-cinnamaldehyde (III),

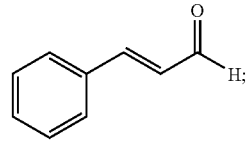

(III)

in the presence of a secondary amine compound; then
(ii) treating the product of the preceding step with acid to afford the compound of formula (I).
The above process may also be used in the production of tolterodine and fesoterodine, which are useful in the treatment of overactive bladder.

22 Claims, No Drawings

PROCESS FOR THE PRODUCTION OF BENZOPYRAN-2-OL DERIVATIVES

This application is a National Stage filing under 35 U.S.C. §371 based on International Application No. PCT/IB2007/001379, filed May 21, 2007, which claims priority to U.S. Provisional Application Ser. No. 60/803,068, filed May 24, 2006.

The present invention relates to an improved process for the production of intermediates useful in the preparation of tolterodine, fesoterodine and other pharmaceutically useful compounds. The invention also provides improved processes for the production of such pharmaceutically useful compounds using the intermediates.

Tolterodine {2-[(1R)-3-[bis(1-methylethyl)amino]-1-phenylpropyl]-4-methylphenol or alternatively (+)-N,N-diisopropyl-3-(2-hydroxy-5-methylphenyl)-3-phenylpropylamine}, is a muscarinic receptor antagonist for the treatment of overactive bladder including urinary incontinence. It gained its first marketing approval (as the tartrate salt) in 1997 and was launched in many markets in the following years under the trade marks DETROL and DETRUSITOL. Tolterodine tartrate was disclosed in International Patent Application WO 89/06644 (see in particular Example 22 and claim 7).

WO 98/29402 discloses a process for the production of tolterodine which comprises condensing p-cresol (a) with cinnamic acid (b), followed by reduction of the resulting lactone (c) with a reducing agent, such as diisobutylaluminium hydride (DIBAL), sodium bis(2-methoxyethoxy) aluminium hydride or lithium tri-tert-butoxyaluminohydride, to give the corresponding benzopyran-2-ol compound (d). The benzopyran-2-ol compound (d) can then be converted to racemic tolterodine hydrochloride (e) by reductive amination with diisopropylamine, followed by addition of aqueous hydrochloric acid. Finally, tolterodine L-tartrate is formed by neutralisation of the hydrochloride salt (e) with NaOH/NaHCO$_3$ and subsequent resolution using L-tartaric acid. The process is shown in Scheme 1 below.

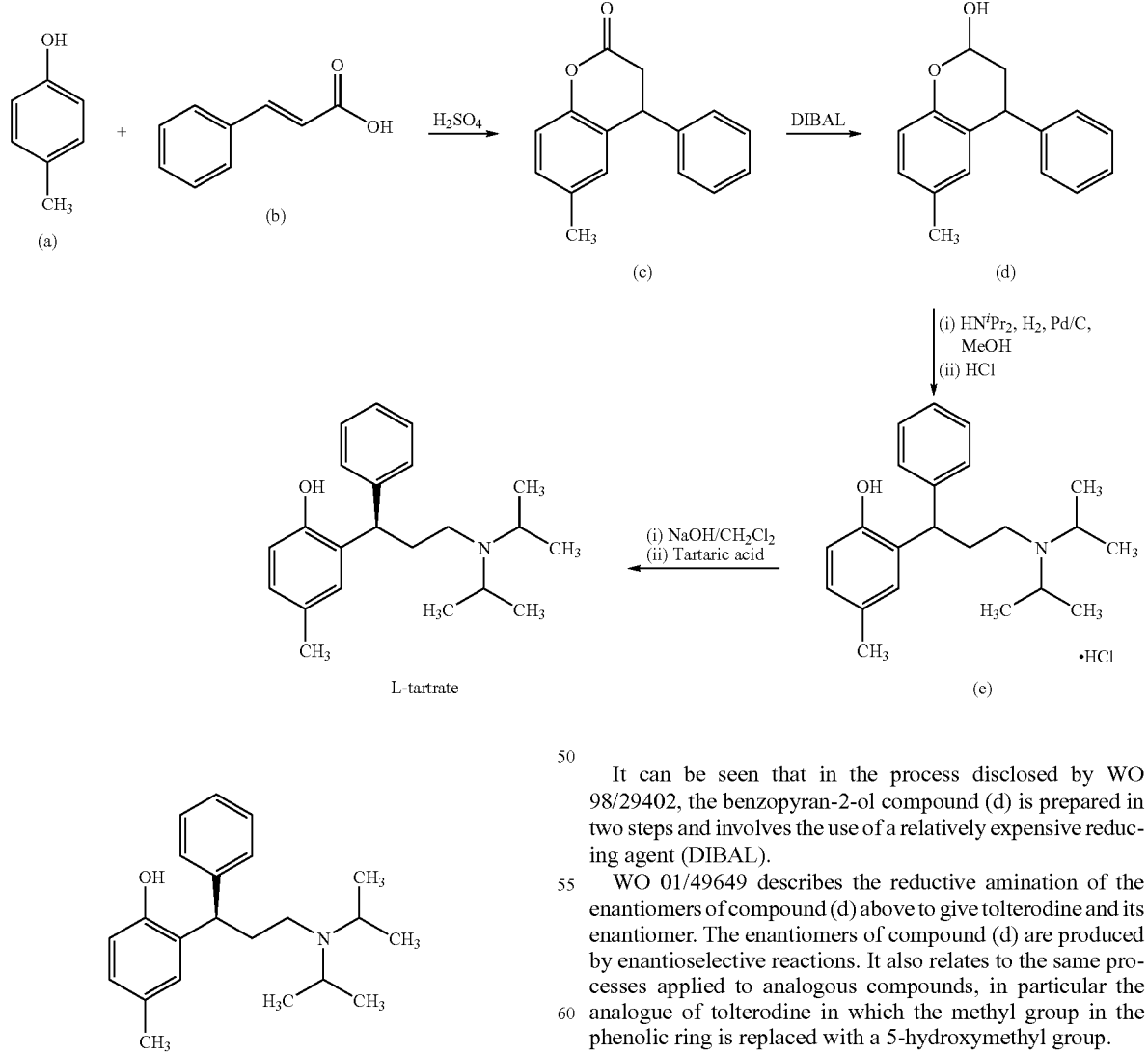

It can be seen that in the process disclosed by WO 98/29402, the benzopyran-2-ol compound (d) is prepared in two steps and involves the use of a relatively expensive reducing agent (DIBAL).

WO 01/49649 describes the reductive amination of the enantiomers of compound (d) above to give tolterodine and its enantiomer. The enantiomers of compound (d) are produced by enantioselective reactions. It also relates to the same processes applied to analogous compounds, in particular the analogue of tolterodine in which the methyl group in the phenolic ring is replaced with a 5-hydroxymethyl group.

US Patent Application 2003/0236438 (MacMillan et al) discloses the use of comparatively complex chiral imidazolidinone catalysts [e.g. (2S,5S)-5-benzyl-2-tert-butyl-3-methylimidazolidin-4-one] for carrying out enantioselective 1,4-addition reactions between aniline nucleophiles and α,β-unsaturated aldehydes (this work is also described in MacMillan et al, *J. Am. Chem. Soc.*, 2002, 124, 7894-7895). Example 2 from US Patent Application 2003/0236438 is typical of the reactions disclosed:

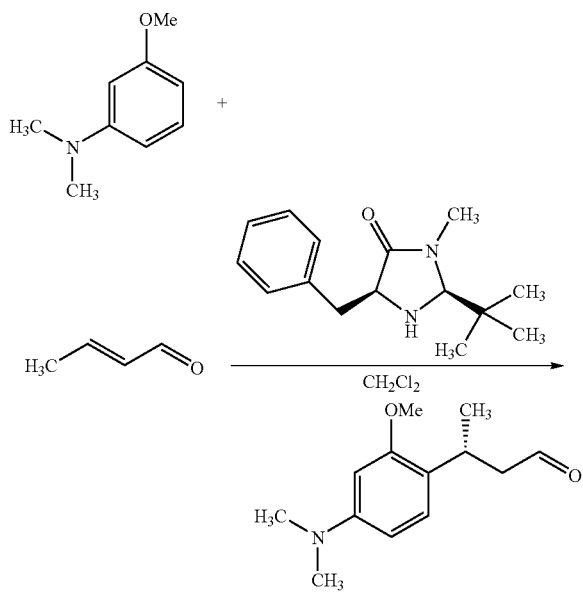

It can be seen that the carbon atom of the aromatic ring para to the amine group bonds to the alpha-beta unsaturated aldehyde.

Jurd (Journal of Heterocylic Chemistry, vol 28 (4), 1991, pp 983-986) describes the reaction of 3,4-methylenedioxyphenol, morpholine and cinnamaldehyde in methanol to produce 2-morpholinyl-4-phenylbenzopyrans.

Surprisingly, it has now been found that the benzopyran-2-ol compound (d) of Scheme 1 can be produced in a one-pot reaction starting from p-cresol (a). Analogous compounds can also be produced. Thus, according to a first aspect of the present invention, there is provided a process for the production of a compound of formula (I),

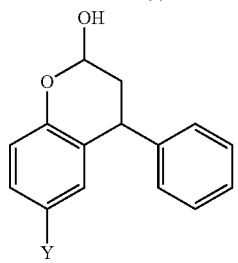

(I)

wherein Y is selected from $CH_3$, $CH_2OH$, $CH_2CH_2OH$, $CH_2Br$ and Br;

comprising the steps of:
(i) reacting a compound of formula (II),

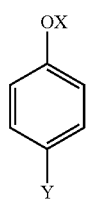

(II)

wherein
OX is hydroxy or $O^-M^+$, in which $M^+$ is a cation selected from $Li^+$, $Na^+$ and $K^+$, and Y is as defined above;
with trans-cinnamaldehyde (III),

(III)

in the presence of a secondary amine compound; then
(ii) treating the product of the preceding step with acid to afford the compound of formula (I).

By "secondary amine compound" we mean an organic compound which contains at least one secondary amine group, i.e. a compound of the formula:

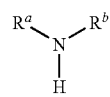

in which $R^a$ and $R^b$ are not hydrogen. Preferably, $R^a$ and $R^b$ are each linked to the nitrogen atom by a $CH_2$ group, for example they are independently $C_{1-6}$ alkyl or together form a 4- or 5-membered alkyl chain in which one carbon atom is optionally replaced by O or N.

Preferred embodiments of the first aspect of the invention are those in which:
(a) OX is hydroxy;
(b) Y is $CH_3$ or $CH_2OH$;
(c) the secondary amine compound is achiral;
(d) the secondary amine compound contains two secondary amine groups, for example piperazine (this catalyst produces particularly high yields);
(e) when the secondary amine compound contains two secondary amine groups, 0.5-1.25 mole equivalents of the secondary amine compound are used in step (i);
(f) alternatively, the secondary amine compound contains one secondary amine group, and more preferably the secondary amine compound is morpholine, dibutylamine, dibenzylamine, 1,1,3,3-tetramethylguanidine, diethylamine, diisopropylamine, piperidine or an N—($C_{1-6}$ alkyl)piperazine. N-methylpiperazine is particularly preferred because it produces good yields, the initial product [see formula (VI) below] is readily hydrolysed to the corresponding lactol compound of formula (I), and the crude compound of formula (I) has an improved purity which facilitates crystallization;
(g) when the secondary amine compound contains one secondary amine group, 1-5, more preferably 1-2.5 mole equivalents of the secondary amine compound are used in step (i);
(h) the acid used in step (ii) is aqueous hydrochloric acid (preferably no more than 2M concentration), although the following aqueous acids at similar concentrations also provide good results: citric acid, acetic acid, oxalic acid, trifluoroacetic acid, maleic acid, fumaric acid, salicyclic acid, trans-cinnamic acid, benzoic acid, camphor sulfonic acid and tosic acid;
(i) the reaction of step (i) is carried out in an organic solvent selected from toluene, xylene, N-butyl acetate, t-amyl alcohol, dioxane and dibutyl ether, most preferably toluene (which produces particularly high yields);

(j) the reaction of step (i) is carried out at a temperature in the range 80° C. to the reflux temperature of the solvent;

(k) the reaction of step (i) is carried out under conditions that remove water from the reaction system (e.g. Dean-Stark conditions, in which water produced by the reaction is condensed in a side condenser so that it does not return to the reaction mixture, and can be drained off if desired); and (l) the reaction of step (i) is carried out at or around ambient pressure (e.g. a nitrogen atmosphere of slightly elevated pressure may be used, particularly on an industrial scale).

It is particularly preferred that when Y is CH$_2$OH, the secondary amine compound is N-methylpiperazine.

Preferably, the secondary amine compound contains two basic nitrogen atoms. Such compounds produce initial products [see formula (VI) below] which hydrolyse readily to compounds of formula (I).

According to a second aspect of the invention, there is provided a process for the production of a compound of formula (IV),

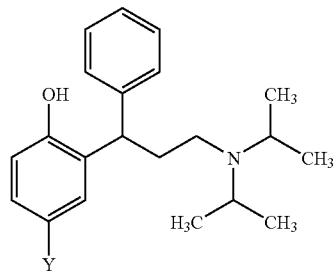

(IV)

wherein Y is selected from CH$_3$, CH$_2$OH, CH$_2$CH$_2$OH, CH$_2$Br and Br, or a salt thereof, comprising:

(a) producing a compound of formula (I) as defined above, using the process according to the first aspect of the invention; then (b) reductively aminating the compound of formula (I) with diisopropylamine;

(c) and where desired converting the resulting compound into a salt.

Preferably, in the second aspect of the invention, Y is CH$_3$ or CH$_2$OH. When Y is CH$_3$, the compound of formula (IV) may be treated with L-tartaric acid in step (c), to produce tolterodine L-tartrate [i.e. R-(+)-tolterodine L-tartrate]. When the compound of formula (IV) is to be used as a pharmaceutical, the salt form produced in this second aspect of the invention is preferably pharmaceutically acceptable. However, when the compound will be processed further, this is not essential.

The reductive amination of a compound of formula (I) may comprise treatment with diisopropylamine in a suitable solvent, such as methanol (which is preferred) or tert-amyl alcohol or mixtures thereof, followed by hydrogenation in the presence of a catalyst, such as Pd/C or Pd(OH)$_2$/C.

In one embodiment, the compound of formula (IV) may be treated with an aqueous acid, such as hydrochloric acid, to afford the corresponding hydrochloride salt. The racemic compound may be converted to the corresponding (R)-enantiomer L-tartrate salt by neutralization of the hydrochloride salt in the presence of base, such as a mixture of sodium hydroxide and sodium carbonate, followed by resolution with L-tartaric acid. In one embodiment, tolterodine L-tartrate [i.e. R-(+)-tolterodine L-tartrate] is prepared.

In an alternative embodiment, the (R)-enantiomer L-tartrate salt of the compound of formula (IV) may be prepared directly following reductive amination of the compound of formula (I) without formation of the hydrochloride salt. For example, in one embodiment the product of the reductive amination step may be treated with a solvent such as acetone and L-tartaric acid to afford the L-tartrate salt. When Y is CH$_3$, this produces tolterodine L-tartrate [i.e. R-(+)-tolterodine L-tartrate].

According to a third aspect, the invention provides a process for the production of fesoterodine,

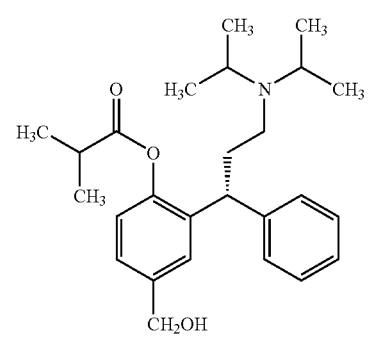

or a pharmaceutically acceptable salt thereof, which comprises:

(a) producing a compound of formula (IV), as defined above in which Y is CH$_2$OH, using the process described above;

(b) resolving the product of step (a) to obtain the (R)-enantiomer;

(c) acylating the phenolic hydroxy group of the product of step (b) to produce the corresponding isobutyric acid ester;

(d) and where desired or necessary, converting the resulting compound into a pharmaceutically acceptable salt.

Fesoterodine, having the chemical name 2-[(1R)-3-[bis(1-methylethyl)amino]-1-phenylpropyl]-4-hydroxymethylphenyl isobutyrate or, alternatively, R-(+)-isobutyric acid 2-(3-diisopropylamino-1-phenylpropyl)-4-hydroxymethylphenyl ester, is disclosed in European Patent 1077912 (see page 32 line 5 and claim 4, 3$^{rd}$ compound). It is indicated in the treatment of overactive bladder.

In this third aspect, the resolution is preferably carried out by fractional crystallization with a chiral acid, preferably (R)-(–)-acetoxy(phenyl)acetic acid.

The acylating agent is preferably isobutyryl chloride.

The compound of formula (I) may exist in an open-ring form, although it is believed to exist predominantly in the closed-ring (lactol) form. Furthermore, it is believed that the process according to the first aspect of the invention produces a mixture of diastereoisomers of the lactol:

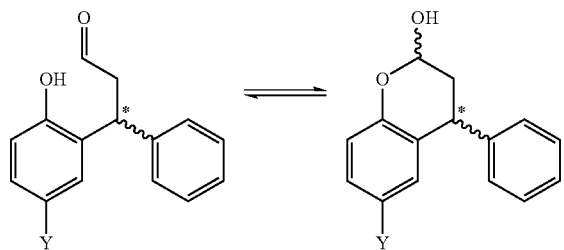

(I)

The R- and S-enantiomers of the chiral centre marked with an asterisk above are believed to be present in equal amounts. The production of all these tautomeric and stereoisomeric forms is embraced by the present invention.

When piperazine is used in step (i) of the first aspect of the invention, the reaction proceeds via an isolable intermediate compound of formula (V),

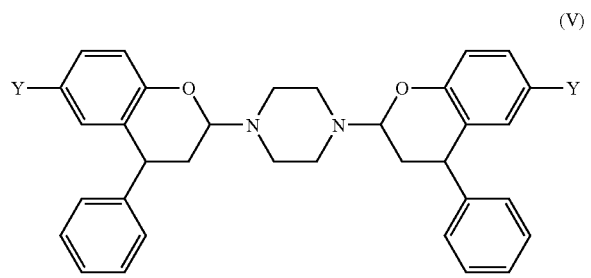

(V)

wherein Y is selected from $CH_3$, $CH_2OH$, $CH_2CH_2OH$, $CH_2Br$ and Br. These compounds are provided according to a fourth aspect of the present invention. Preferably, Y is $CH_3$.

When N-methylpiperazine is used in step (i) of the first aspect of the invention, the reaction proceeds via an intermediate compound of formula (VI)

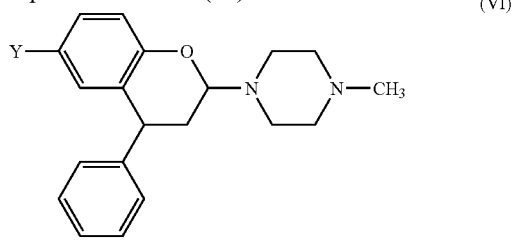

(VI)

wherein Y is selected from $CH_3$, $CH_2OH$, $CH_2CH_2OH$, $CH_2Br$ and Br. These compounds are provided according to a fifth aspect of the present invention. Preferably, Y is $CH_2OH$.

The invention further provides a compound of formula (I),

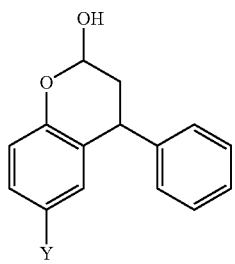

wherein Y is selected from $CH_2CH_2OH$, $CH_2Br$ and Br.

The process according to the invention differs from U.S. Patent Application 2003/0236438 (see above) in that none of the reactants are an aniline compound, and the compound of formula (II) according to the invention does not have an additional strongly activating or strongly electron-donating group present (such as methoxy in Example 2 of U.S. Patent Application 2003/0236438). Furthermore, the amine catalysts used in the present invention are much simpler (e.g., they do not need to be chiral) and hence cheaper.

The process according to the invention differs from the Jurd paper mentioned above in that none of the reactants are an aniline compound, and the compound of formula (II) according to the invention does not have an additional strongly activating or strongly electron-donating group present, such as alkoxy or hydroxy.

The invention has the further advantage that, as part of a process for the production of tolterodine, in comparison with the process disclosed by WO 98/29402, a number of reaction and processing steps are eliminated, leading to a reduction in costs. Furthermore, the process avoids the use of expensive reducing agents such as diisobutylaluminium hydride (DIBAL), sodium bis(2-methoxyethoxy)aluminium hydride or lithium tri-tert-butoxyaluminohydride, which are also difficult to dispose of.

The invention has the further advantage that, as part of a process for the production of fesoterodine, in comparison with the processes disclosed in the prior art, a number of reaction and processing steps are eliminated, leading to a reduction in costs. Furthermore, the process avoids the use of hazardous and environmentally undesirable reagents, which are difficult to dispose of.

The invention is illustrated by the following examples in which the following abbreviations may be used:

BuOH=butanol
DEA=diethylamine
DMA=dimethylacetamide
DMF=dimethylformamide
DMPU=1,3-dimethyl-3,4,5,6-tetrahydro-2(1H)-pyrimidone
DMSO=dimethylsulphoxide
EDTA=ethylenediaminetetraacetic acid
ee=enantiomeric excess
EtOAc=ethyl acetate
EtOH=ethanol
h=hour
IPA=isopropyl alcohol
LC-MS=liquid chromatography—mass spectrometry
LOD=loss on drying
MeOH=methanol
min=minute
n-BuOH=n-butanol
p.s.i.=pounds per square inch
TFA=trifluoroacetic acid
THF=tetrahydrofuran
tlc=thin layer chromatography

EXAMPLE 1

Synthesis of 3,4-Dihydro-6-methyl-4-phenyl-2H-benzopyran-2-ol

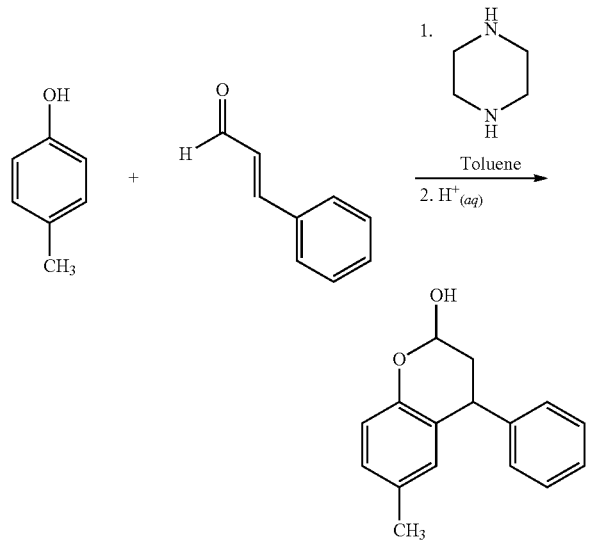

p-Cresol (150 g, 1.387 mol) was stirred with piperazine (72 g, 0.832 mol, 0.6 eq) in toluene (1.5 L, 10 ml/g) and then heated at reflux under Dean & Stark conditions for at least 30 minutes to remove water giving a clear pale yellow solution. Trans-Cinnamaldehyde (262 ml, 275 g, 2.081 mol, 1.5 eq) was then added over 2 hours whilst maintaining the reaction mixture at reflux under Dean & Stark conditions. Once the addition was complete, heating of the reaction mixture was continued at reflux under Dean & Stark conditions for a further 4 hours. The black solution was allowed to cool to 80° C. and then slowly quenched over 45 minutes with a solution of 0.67M $HCl_{(aq)}$ (750 ml, 0.601 mol, 1.3 eq). The two-phase solution was then stirred vigorously for at least 12 hours at a temperature of 75-80° C. The stirring was then stopped and the mixture allowed to cool to room temperature and the phases separated. The toluene solution was then washed with 1M $HCl_{(aq)}$ (750 ml, 5 ml/g), then water (3×750 ml, 5 ml/g). The 3,4-dihydro-6-methyl-4-phenyl-2H-benzopyran-2-ol was not isolated but instead the toluene solution was used directly in the reductive amination step (Example 2).

EXAMPLE 2

Synthesis of Tolterodine L-Tartrate

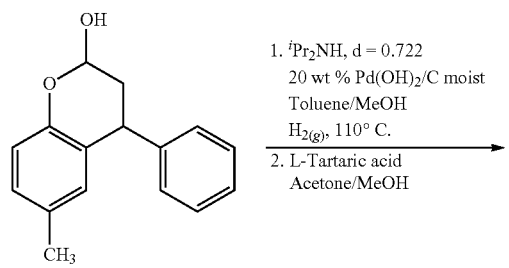

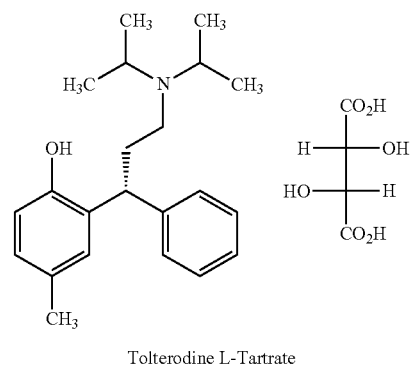

Tolterodine L-Tartrate

The toluene solution comprising crude 3,4-dihydro-6-methyl-4-phenyl-2H-benzopyran-2-ol from Example 1 (theoretical=333.3 g in 1.5 L of toluene) was diluted with methanol (750 ml, 5 ml/g), then diisopropylamine (583 ml, 421 g, 4.161 mol, 3 eq) was added. The black solution was then hydrogenated over 20 wt % $Pd(OH)_2$/C moist (10 wt %, 33 g) at $621 \times 10^3$ $Nm^{-2}$ (90 psi) and 110° C. for 48 hours. A sample was removed for analysis.

The reaction mixture was filtered through Arbocel™ (filter aid) to remove catalyst residues and then heated to reflux and all diisopropylamine and methanol removed by distillation and replaced with toluene resulting in a final volume of 10 ml/g. The black solution was then cooled to 25° C., acetone (750 L, 5 ml/g) was added, and then the solution heated to 55-60° C. A solution of L-Tartaric acid (312 g, 2.081 mol, 1.5 eq) in methanol (1.05 L, 7 ml/g) was added over 30 minutes maintaining the temperature at 55-60° C. The resulting suspension was then allowed to cool to room temperature and stirred for 12 hours. The suspension was filtered, washed with acetone (2×600 ml, 4 ml/g), then dried in a vacuum oven at 50° C. for 12 hours to give the title compound as an off white solid [159.2 g, 48% (24% from p-Cresol)]. Achiral purity was 100% (no impurities detected) and chiral purity was 91.4% e.e.

EXAMPLE 3

Synthesis of Racemic Tolterodine Hydrochloride

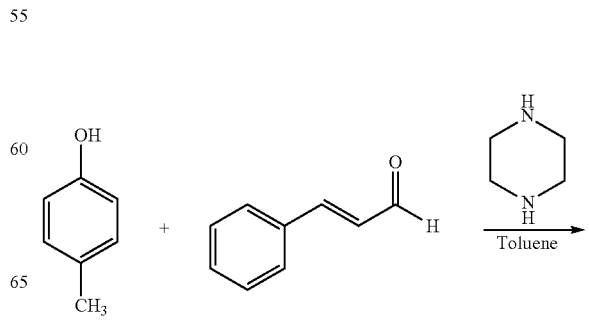

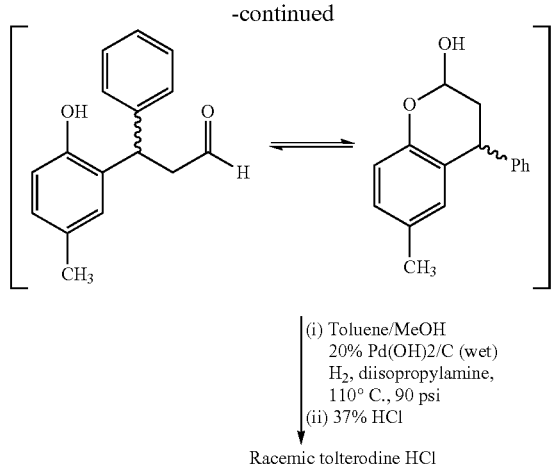

(i) Toluene/MeOH
   20% Pd(OH)2/C (wet)
   H₂, diisopropylamine,
   110° C., 90 psi
(ii) 37% HCl Racemic tolterodine HCl

Step A. Preparation of 3,4-Dihydro-6-methyl-4-phenyl-2H-benzopyran-2-ol

To a solution of p-cresol (25 g, 0.231 mol, 1 equiv), piperazine (11.94 g, 0.139 mol, 0.6 equiv) and toluene (250 ml, 10 ml/g) at reflux under Dean & Stark conditions was added cinnamaldehyde (45.83 g, 44 ml, 0.347 mol, 1.5 equiv) over a 2 hour period and reaction mixture monitored by HPLC for the presence of p-cresol. Upon completion (2 to 3 hours), the mixture was cooled to 80° C. and a solution of c.HCl (25 ml, 0.301 mol, 1.3 equiv) in water (100 ml, 5 ml/g) was slowly added and heated at 80-90° C. for at least 5 hours. The resulting solution was allowed to cool to room temperature and the phases separated. The toluene solution was washed with 1M HCl (125 ml, 5 ml/g), then water (3×125 ml). The resulting organic layer was taken into the reductive amination step (Step B) as a crude mixture.

Step B. Preparation of Racemic Tolterodine Hydrochloride

To the crude solution from Step A was added methanol (125 ml, 5 ml/g cresol) and diisopropylamine (92 ml, 0.693 mol, 3 equiv). The mixture was then hydrogenated over 20 wt % Pd(OH)₂/C wet (5.6 g, 10 wt % theory of the benzopyran-2-ol) at 110° C. under $586 \times 10^3$ Nm$^{-2}$ (85 psi) hydrogen pressure. Reaction progress was monitored by HPLC (completion usually occurs between 16 and 24 h). Upon completion, the mixture was cooled, purged with nitrogen, filtered and washed with toluene (2×25 ml). The filtrate was then azeotroped with toluene to remove all methanol and diisopropylamine to end at a final volume corresponding to 10 ml/g cresol. The solution was then stirred at 50-60° C. and 37% HCl (19.3 ml, 0.231 mol, 1.0 equiv c.f cresol) was added resulting in the precipitation of racemic tolterodine hydrochloride. The suspension was cooled to 25° C. and stirred for 2 h, then filtered and washed with toluene (2×50 ml). Racemic tolterodine hydrochloride was then dried under vacuum at 50° C. Yield was 52.7 g, 63% from p-cresol with achiral purity of 97%.

The synthesis of tolterodine L-tartrate according to the methods of Examples 1-3 is shown in Scheme 2 below.

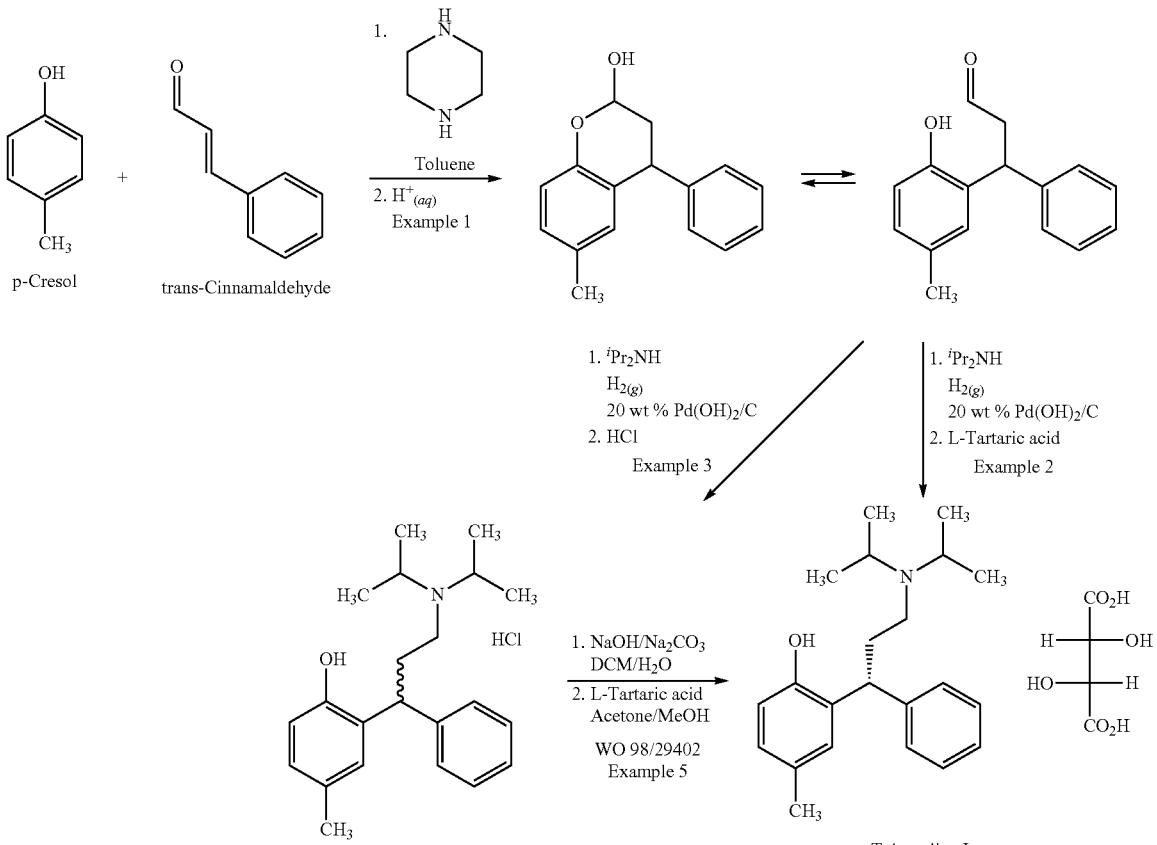

EXAMPLE 4

Influence of amine catalyst and solvent on yield of 3,4-Dihydro-6-methyl-4-phenyl-2H-benzopyran-2-ol The reaction of Example 1 was repeated, but varying the amine catalyst and the solvent. The temperature used was approximately 100° C. or the reflux temperature of any solvent if lower (unless indicated otherwise). Dean-Stark conditions were not used unless indicated (by *). The yields are shown in the following table.

| Amine catalyst | Solvent | Yield (HPLC in-situ unless specified) |
| --- | --- | --- |
| R-(+)-α-methylbenzylamine | None (neat rxn) | 13% (9% isolated) |
| Ammonia | None (neat rxn) | 0% |
| (S)-(+)-2-amino-1-propanol | None (neat rxn) | 0% |
| Piperidine† | None (neat rxn) | 24% |
| Diisopropylamine† | None (neat rxn) | 32% |
| Pyrrolidine† | DMF | 0% |
| Morpholine† | None (neat rxn) | 54% (48% isolated) |
| proline† | None (neat rxn) | 0% |
| 'MacMillans base'† (2S,5S)-5-benzyl-2-tert-butyl-3-methylimidazolidin-4-one [0° C. to ambient temperature] | DCM | 0% |
| Piperazine*† | Toluene | 68% |
| Piperazine*† | n-butyl acetate | 65% |
| Piperazine*† | t-amyl alcohol | 62% |
| Piperazine† | dibutylether | 61% |
| Piperazine† | dioxane | 74% |
| Piperazine† | THF | 0% |
| Tri-n-butylamine | Toluene | 8% |
| N-methylmorpholine with cat piperazine | Toluene | 12% |
| N-methyldicyclohexylamine with cat piperazine | Toluene | 6% |
| N-Ethyldiisopropylamine with cat piperazine | Toluene | 5% |
| Pyridine with cat piperazine | Toluene | 8% |
| Triethanolamine with cat piperazine | Toluene | 4% |
| t-butyl(1S,4S)-(−)-2,5 diazabicyclo[2.2.1]-heptane-2-carboxylate† | Toluene | 3% |
| (R)-1-Benzoyl-3-methylpiperazine† | Toluene | 8% (5% isolated) |
| Diethylamine† | Toluene | 45% |
| Aniline | di-butylamine | 4% |
| cyclohexylamine | DMAc | 2% |

†denotes secondary amine compound

EXAMPLE 5

1,4-Bis-(6-methyl-4-phenyl-chroman-2-yl)-piperazine

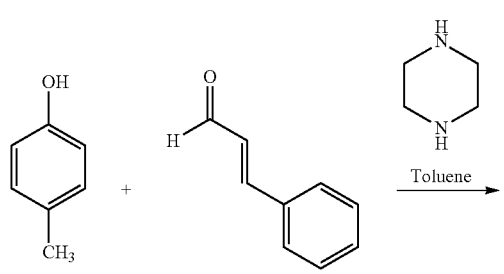

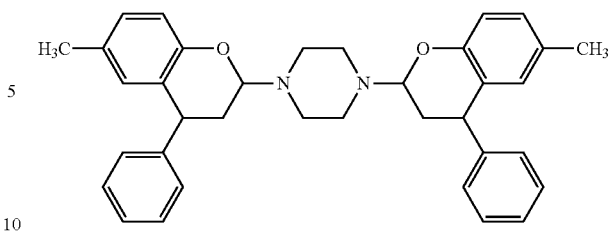

The preparation of the title compound was carried out using the procedure of Example 1, except for the omission of a quench with aqueous acid. Instead, upon completion of the reaction the mixture was allowed to cool to ambient temperature resulting in a brown suspension. Filtration of this suspension gave a brown solid with $^1$H and $^{13}$C NMR providing confirmation of the structure. Melting point: 241° C.

EXAMPLE 6

Preparation of 6-(2-Hydroxy-ethyl)-4-phenyl-chroman-2-ol

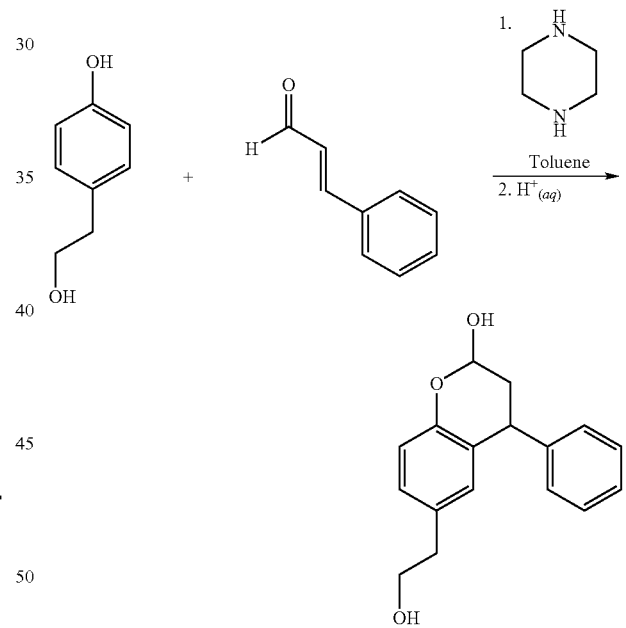

To a solution of 4-hydroxyphenethyl alcohol (Tyrosol) (5.0 g, 36 mmol, 1 equiv), piperazine (1.87 g, 22 mmol, 0.6 equiv) and toluene (50 ml) at reflux under $N_2$ and Dean & Stark conditions was added cinnamaldehyde (6.4 ml, 51 mmol, 1.4 equiv) and the reaction mixture maintained at heat for 17 h. The reaction was cooled to 80° C. and quenched with aqueous HCl (0.7 molar, 1.3 equiv) then stirred at heat for 18 h. The biphasic mixture was allowed to cool to ambient temperature, separated, the organic phase washed with aqueous HCl and water and the organic phase concentrated to a black residue under reduced pressure. Flash chromatography eluting with 20% EtOAc/Heptane afforded the title compound as the main constituent of an approximately 80% pure yellow oil, $R_f$=0.37 (50% EtOAc/Heptane) and structure confirmed by $^1$H NMR and LC-MS (M+1=271).

EXAMPLE 7

Alternative preparation of 6-(2-hydroxy-ethyl)-4-phenyl-chroman-2-ol using N-methylpiperazine

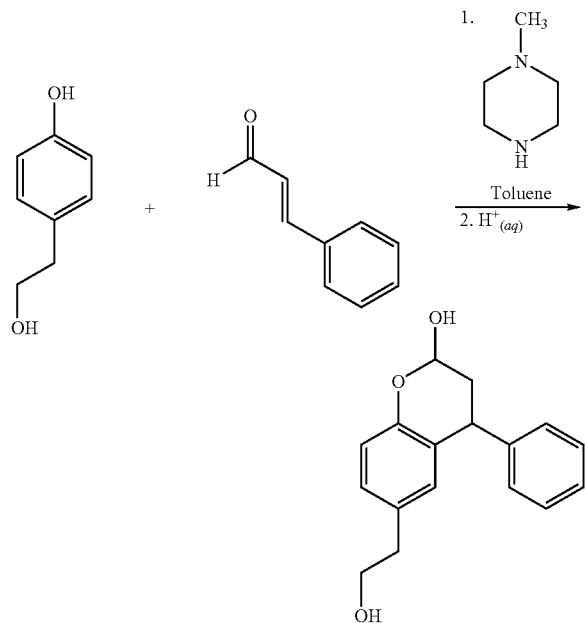

To a solution of 4-hydroxyphenethyl alcohol (Tyrosol) (25.0 g, 181 mmol, 1 equiv), N-methylpiperazine (54.4 g g, 543 mmol, 3 equiv) and toluene (200 ml) at reflux under $N_2$ and Dean & Stark conditions was added cinnamaldehyde (35.9 g ml, 272 mmol, 1.5 equiv) over a period of 2 hours and the reaction mixture maintained at reflux for 17 h. The reaction was cooled to 50° C. and quenched with aqueous HCl (2M, 375 mL, ~4 equiv). The biphasic mixture was allowed to cool to ambient temperature, diluted with ethyl acetate (250 mL) and the organic phase separated. The organic phase was washed with aqueous HCl (250 mL), potassium bicarbonate (1M, 250 mL), dried over magnesium sulphate and evaporated under reduced pressure to give a black oil (50.0 g, assumed to be quantitative).

EXAMPLE 8

Preparation of 2-[3-(Diisopropylamino)-1-phenyl-propyl]-4-(2-hydroxyethyl)phenol hydrochloride

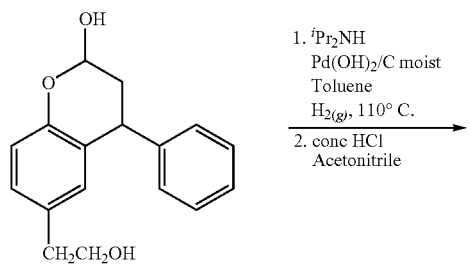

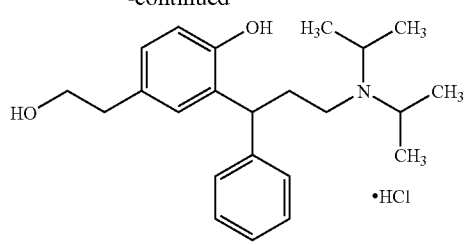

A mixture of 6-(2-hydroxy-ethyl)-4-phenyl-chroman-2-ol (Example 7, 30 g, 111 mmol, 1 equiv), diisopropylamine (33.7 g, 333 mmol, 3 eq) and palladium hydroxide on carbon [50% wet catalyst (50% by weight is water), 6 g, 0.2 equiv] in toluene (120 mL) was hydrogenated at $621 \times 10^3$ $Nm^{-2}$ (90 psi) hydrogen pressure at 110° C. The reaction mixture was cooled to room temperature and filtered through arbocel and evaporated under reduced pressure. The resulting oil was dissolved in acetonitrile (200 mL) and concentrated hydrochloric acid (11.6 mL, 1.05 equiv) was added. The mixture was distilled at ambient pressure, removing approximately 100 mL of acetonitrile, and the distilled solvent replaced with fresh acetonitrile. The mixture was allowed to cool and crystallise overnight. The product was filtered and washed with a small portion of acetonitrile and dried overnight in vacuo at 50° C. to give the title compounds as a white solid (26.7 g, 68.1 mmol, 61%).

EXAMPLE 9

Preparation of 2-[3-(diisopropylamino)-1-phenylpropyl]-4-(2-hydroxyethyl)phenol

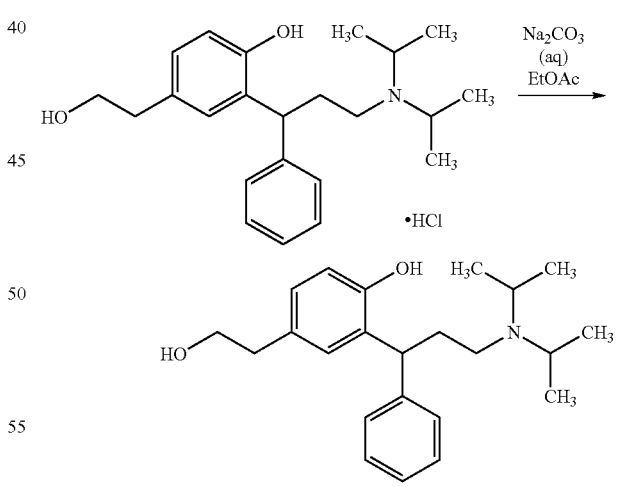

Aqueous sodium bicarbonate (165 mL) was added to a mixture of the HCl salt (Example 8, 16.5 g, 42.1 mmol, 1 equiv) in ethyl acetate (165 mL) and the mixture stirred for 1 hour. The phases were separated and the organic phase washed with water (195 mL), dried over magnesium sulphate and evaporated under reduced pressure to give the title compound as an oil containing ~25% wt/wt ethyl acetate (14.6 g total, 11.03 g of title compound, 31 mmol, 74%).

EXAMPLE 10

Preparation of (R)-2-[3-(Diisopropylamino)-1-phenylpropyl]-4-(2-hydroxyethyl)phenol (S)-2-phenoxypropionic acid salt

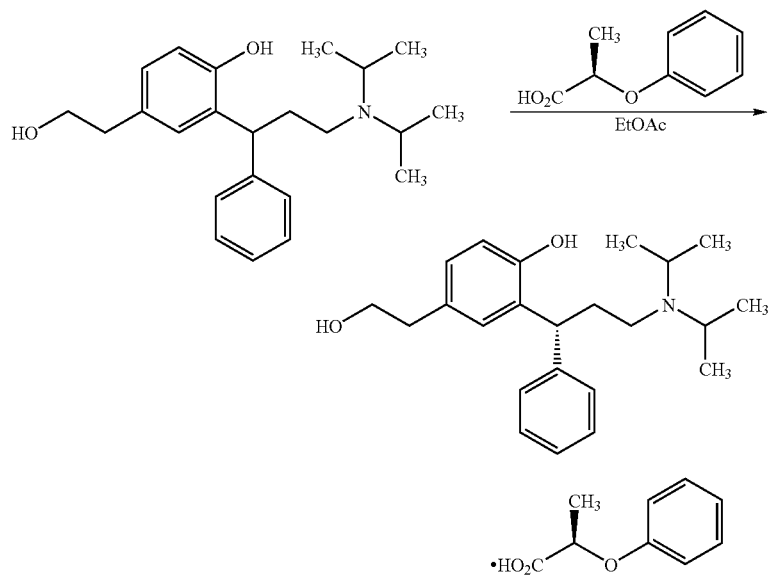

(S)-2-Phenoxypropionic acid (3.40 g, 20.5 mmol, 1 equiv) was added to a solution of 2-[3-(diisopropylamino)-1-phenylpropyl]-4-(2-hydroxyethyl)phenol (Example 9, 7.28 g, 20.5 mmol, 1 equiv) in ethyl acetate. The mixture was heated at 80° C. for 2 days, upon which the mixture was cooled to room temperature, filtered and washed with ethyl acetate and dried in vacuo at 50° C. overnight to give the title compound as a white solid (3.9 g, 7.48 mmol, 37% yield, 94% ee).

Enantiomeric excess was determined by converting the salt to the free base with sodium hydroxide and running normal phase chiral HPLC chromatography (Chiral Pak AS-H column, eluting with hexane (89.8%), IPA (10%), DEA (0.1%), TFA (0.1%) at 1 mL/minute).

The title compound could be useful as a starting material to produce Example 5 in our co-pending International Patent Application No PCT/IB07/000619. The corresponding hydrochloride salt to the title compound is disclosed as Example 12 in WO 98/43942.

EXAMPLE 11

Synthesis of 3,4-dihydro-6-bromo-4-phenyl-2H-benzopyran-2-ol

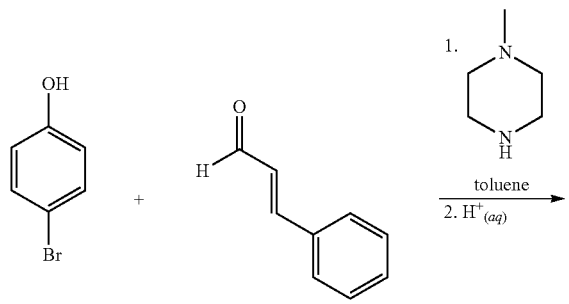

-continued

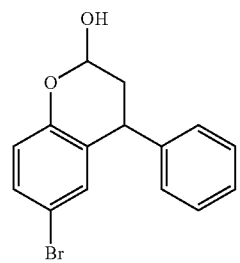

4-Bromophenol (2.0 g, 11.6 mmol) was stirred with N-methylpiperazine (3.48 g, 34.8 mmol, 3 eq) in toluene (30 ml, 15 ml/g) and heated at reflux under Dean & Stark conditions. Once reflux was achieved, trans-cinammaldehyde (2.2 g, 17.4 mmol, 1.5 eq) was added over 2 hours. Once addition was complete, heating of the reaction mixture at reflux under Dean & Stark conditions was continued for 3 hours. The dark solution was cooled to 25° C. and diluted with ethyl acetate (20 ml, 10 ml/g) and quenched with 2M HCl (30 ml, 15 ml/g). The phases were separated and the upper organic layer was washed with further 2M HCl (20 ml, 10 ml/g) and 1M sodium hydrogen carbonate solution (20 ml, 10 ml/g). The organic phase was dried (MgSO₄), filtered and concentrated to give a dark coloured oil (4.2 g, 11.6 mmol, assumed to be quantitative)

EXAMPLE 12

Synthesis of 2-[3-(Diisopropylamino)-1-phenylpropyl]-4-bromophenol hydrochloride salt

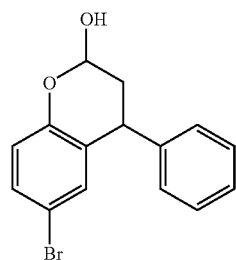

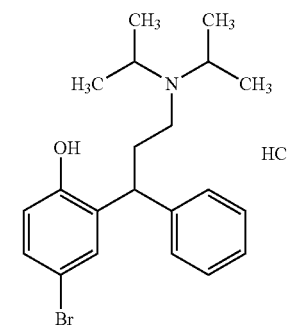

Crude 3,4-dihydro-6-bromo-4-phenyl-2H-benzopyran-2-ol (Example 11, 2.0 g, 6.55 mmol) was dissolved in toluene (20 ml, 10 ml/g) and to this solution was added titanium tetraisopropoxide (5.84 ml, 3 eq) and diisopropylamine (1.0 ml, 1.1 eq). The reaction mixture was cooled to 0-5° C. and sodium borohydride (0.75 g, 3 eq) was added portionwise over 15 minutes. Ethanol was charged dropwise over 15 minutes and stirred at 0-5° C. for a further 2 hours. The reaction was quenched with water (20 ml), ethyl acetate (50 ml) and concentrated ammonia solution (20 ml). The suspension was filtered through celite and the phases were separated. The organic layer was washed with water (50 ml), dried (MgSO$_4$), filtered and concentrated to give the free base as a brown oil. This was dissolved in ethyl acetate (50 ml) and 5M HCl (2 ml) was added. Excess acid and water were azeotroped with fresh ethyl acetate (2×50 ml) and the resulting solid was granulated in fresh ethyl acetate (20 ml) for 48 hours. The solid was collected by filtration, washed with ethyl acetate (10 ml) and dried at 50° C. under vacuum for 4 hours. The title compound was obtained as a white solid (1.12 g, 40% from 4-bromophenol).

The benzyloxy analogue of the title compound is disclosed as Example 1(e) in WO 94/11337. The title compound, once resolved, could also be useful as a starting material in the production of Example 3 in our co-pending International Patent Application No PCT/IB07/000619.

EXAMPLE 13

Synthesis of (2-Hydroxy-4-phenyl-3,4-dihydro-2H-chromen-6-yl)methanol

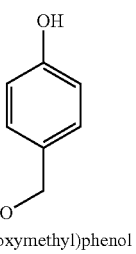

4-(Hydroxymethyl)phenol

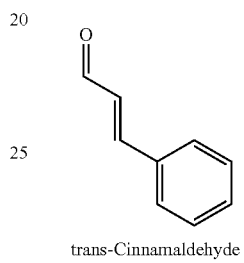

trans-Cinnamaldehyde

N-methylpiperazine
1) Toluene, reflux, 10 h
2) Toluene, EtOAc, HCl 2M wash
3) Toluene, EtOAc, Crystallisation

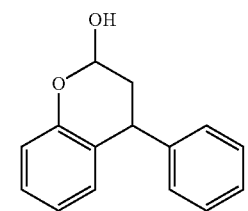

(2-Hydroxy-4-phenyl-3,4-dihydro-2H-chromen-6-yl)methanol 4-(Hydroxymethyl)phenol (2.515 kg, 20.26 mol, 1 eq) was stirred with N-methylpiperazine (5.06 kg, 50.52 mol, 2.5 eq) in toluene (17.74 kg, 20.5 L, 8.15 mL/g) and then heated to reflux. trans-Cinnamaldehyde (3.35 kg, 25.35 mol, 1.25 eq) was then added over 2 hours maintaining the reaction mixture at reflux. The transfer line was washed with toluene (0.9 Kg, 0.35 ml/g). Once the addition was complete the reaction mixture continued to be heated at reflux for 19 h. Then some toluene was distilled off, reducing the volume to approximately 18.5 L. The mixture was then allowed to cool to room temperature and EtOAc was added (13.5 Kg 15 L, 6 mL/g). The organic phase was washed with HCl 2M (46.4 kg, 46.4 L 18.5 mL/g). The phases were separated, and ethyl acetate (27.1 kg, 30 L, 12 ml/g) was added to dilute the organic layer. The organic phase was washed with 1M HCl (17.75 kg, 17.75 L 7.1 mL/g), 5% w/w NaHCO$_3$ (17.5 L, 7 mL/g) and water (25 L, 10 mL/g). The phases were separated, and toluene (6.5 Kg, 7.5 L, 3 ml/g) was added to the organic layer, and the mixture was distilled to approximately 8 L. Additional toluene (7 kg) was charged followed by ethyl acetate (3.9 L). The mixture was heated to reflux then cooled to 22° C. at 1° C./minute, then stirred for 20 hrs. The suspension was cooled to 2° C. and granulated for 2 hrs. The slurry was filtered and the cake was washed with cold toluene (2×4.3 Kg, 5 L). The resulting pale tan solid was dried in vacuum for 68 h at 40° C., to provide 2.76 Kg of product (2-hydroxy-4-phenyl-3,4-dihydro-2H-chromen-6-yl)methanol (53.4% yield) which was used in the following example without purification:

$^1$H NMR 300 MHz d6 DMSO δ ppm (mixture of isomers, 10:1): 1.95-2.10 (m, 2H), 2.15-2.35 (m, minor isomer), 3.25-3.35 (m, 1H), 4.15-4.35 (m, 3H), 4.80-4.95 (m, 1H), 5.35-5.45 (m, minor isomer), 5.46-5.55 (m, 1H), 6.51-6.54 (m, minor isomer), 6.58-6.63 (m, 1H), 6.75 (d J=8.2 Hz, 1H), 6.98-7.40 (m, 6H).

EXAMPLE 14

Synthesis of 2-[3-(diisopropylamino)-1-phenylpropyl]-4-(hydroxymethyl)phenol

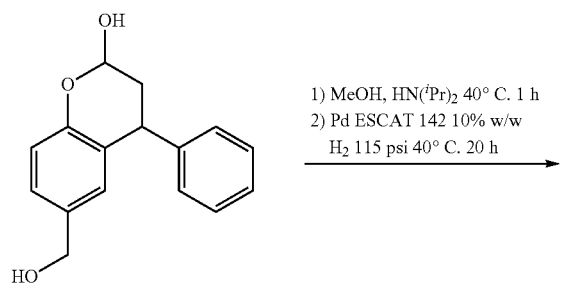

(2-Hydroxy-4-phenyl-3,4-dihydro-2H-chromen-6-yl)methanol

1) MeOH, HN($^i$Pr)$_2$ 40° C. 1 h
2) Pd ESCAT 142 10% w/w H$_2$ 115 psi 40° C. 20 h

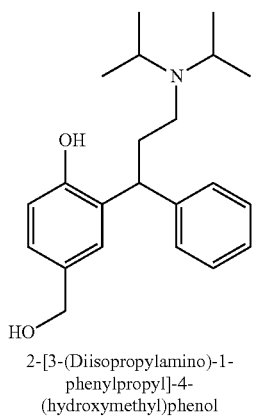

2-[3-(Diisopropylamino)-1-phenylpropyl]-4-(hydroxymethyl)phenol (2-Hydroxy-4-phenyl-3,4-dihydro-2H-chromen-6-yl) methanol (Example 13, 830 g, 3.24 mol, 1.0 eq) was stirred in methanol (4150 mL, 5.0 mL/g). Diisopropylamine (1362 mL, 9.72 mol, 3.0 eq) was then added over 15 minutes via dropping funnel. The resulting solution was then stirred for one hour under nitrogen.

The catalyst Pd-ESCAT 142 [(5% Pd/C paste, ca. 50% water wet) 83 g, 10% w/w] was added as a slurry in methanol (2075 mL, 2.5 mL/g). The system was purged with hydrogen, then the mixture was hydrogenated at 115 psi (793×10$^3$ Nm$^{-2}$, 7.92 bar) at a temperature of 40° C. for 20 hours.

The mixture was purged with nitrogen and filtered over Arbocel™ (filter aid). The residue pad was washed with methanol (2×1660 mL, 2×2.0 mL/g).

Due to equipment limitations, the above procedure was performed two further times on 830 and 840 g scale.

The three filtrates and their respective pad-washes were then combined to produce a single solution equivalent to a single 2.50 Kg scale reaction. The total volume was noted to act as the initial target volume in the following distillation procedure:

Diisopropylamine (2500 mL, 1.0 mL/g) and t-amyl alcohol (10000 mL, 4.0 mL/g) were added to the reaction mixture. A vacuum distillation (100 mbar vacuum set) was then performed to distil down to the target volume previously noted.

Diisopropylamine (2500 mL, 1.0 mL/g) and t-amyl alcohol (10000 mL, 4.0 mL/g) were added to the reaction mixture. A vacuum distillation (100 mbar vacuum set) was then performed to distil down to the target volume previously noted.

Diisopropylamine (2500 mL, 1.0 mL/g) and t-amyl alcohol (10000 mL, 4.0 mL/g) were added to the reaction mixture. A vacuum distillation (100 mbar vacuum set) was then performed to distil down to the target volume previously noted.

t-Amyl alcohol (12500 mL, 5.0 mL/g) was added to the reaction mixture. A vacuum distillation (100 mbar vacuum set) was then performed to distil down to a volume of 12500 mL.

t-Amyl alcohol (12500 mL, 5.0 mL/g) added to the reaction mixture. A vacuum distillation (100 mbar vacuum set) was then performed to distil down to a volume of 12500 mL. t-Amyl alcohol (12500 mL, 5.0 mL/g) added to the reaction mixture to give a final volume of 25 L.

The t-amyl alcohol solution of crude product 2-[3-(diisopropylamino)-1-phenylpropyl]-4-(hydroxymethyl)phenol was used in the next step with no further purification. HPLC analysis (area/area) showed 93.3% product, plus: 4.2% starting material, and other impurities at 1.4% and 0.4%. Quantitative HPLC analysis indicated the crude solution contained 2950 g product (89% yield).

EXAMPLE 15

Synthesis of (R)-2-[3-(Diisopropylamino)-1-phenylpropyl]-4-(hydroxymethyl)phenol (R)-acetoxy(phenyl)acetate

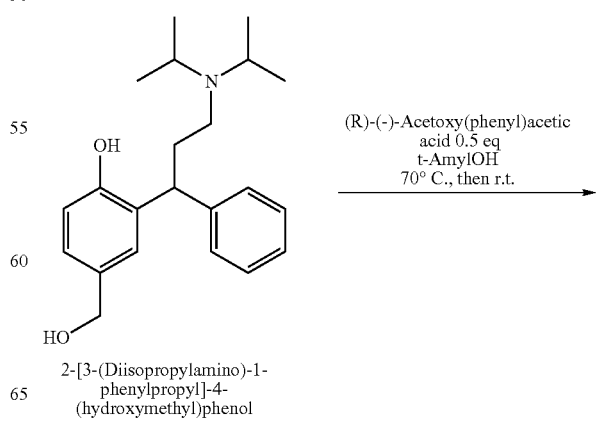

2-[3-(Diisopropylamino)-1-phenylpropyl]-4-(hydroxymethyl)phenol (R)-(-)-Acetoxy(phenyl)acetic acid 0.5 eq
t-AmylOH
70° C., then r.t.

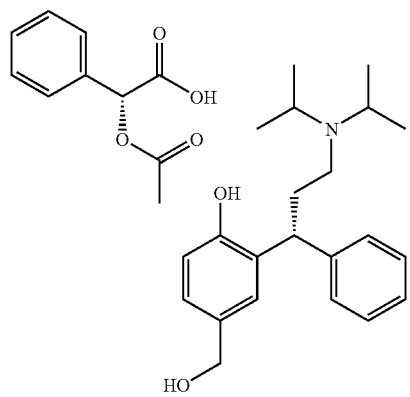

(R)-2-[3-diisopropylamino)-1-phenylpropyl]-4-
(hydroxymethyl)phenol (R)-acetoxy(phenyl)acetate t-Amyl alcohol (19.2 L) was added to the previous solution of 2-[3-(diisopropylamino)-1-phenylpropyl]-4-(hydroxymethyl)phenol (from Example 14) in t-amyl alcohol (25 L, containing 2.95 kg, 8.64 mol, 1 eq) to give a total volume of 44.2 L. This solution was heated to 70° C. In a separate pot, a solution of (R)-(−)-acetoxy(phenyl)acetic acid (0.839 kg, 4.32 mol, 0.5 eq) in t-amyl alcohol (14.8 L) was prepared at 50° C. then cooled to room temperature once all the acid had dissolved. This solution was then added to the solution of 2-[3-(diisopropylamino)-1-phenylpropyl]-4-(hydroxymethyl)phenol in t-amyl alcohol over one hour. The resulting solution was then seeded with product (0.03 kg, 1 wt %, prepared previously by a similar method but on a smaller scale). The slurry was cooled to 60° C. over 2 hours and then to 25° C. over another 3 hours. The mixture was stirred at 25° C. for an additional 12 hours. The slurry was filtered and the cake was twice re-slurried with t-amyl alcohol (2×29.5 L, 2×10 mL/g) and de-liquored well. The white solid was dried under reduced pressure at 40° C. for 12 hours to provide 2.04 kg (R)-2-[3-(diisopropylamino)-1-phenylpropyl]-4-(hydroxymethyl)phenol (R)-acetoxy(phenyl)acetate (37.8% yield, corrected for 14.3% w/w t-amyl alcohol (determined by LOD analysis) with 99% ee by chiral HPLC.

HPLC Method for ee Monitoring:

Column: Chiralpak AS-H

Flow rate: 1 ml/min

Mobile Phase Heptane 92.5/Ethanol 7.5/Diethylamine 0.12/Trifluoroacetic acid 0.18

Temperature: 35° C.

Detection: 220 nm

Retention times:

(R)-2-[3-(diisopropylamino)-1-phenylpropyl]-4-(hydroxymethyl)phenol 15 min (S)-2-[3-(diisopropylamino)-1-phenylpropyl]-4-(hydroxymethyl)phenol 18.4 min

EXAMPLE 16

Synthesis of (R)-2-[3-(Diisopropylamino)-1-phenyl-propyl]-4-(hydroxymethyl)phenol

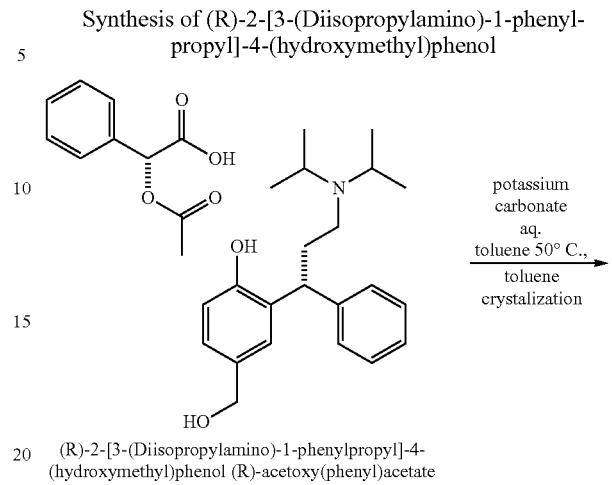

(R)-2-[3-(Diisopropylamino)-1-phenylpropyl]-4-(hydroxymethyl)phenol (R)-acetoxy(phenyl)acetate

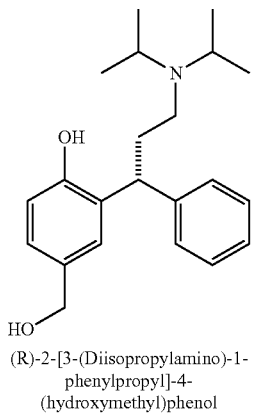

(R)-2-[3-(Diisopropylamino)-1-phenylpropyl]-4-(hydroxymethyl)phenol (R)-2-[3-(diisopropylamino)-1-phenylpropyl]-4-(hydroxymethyl)phenol (R)-acetoxy(phenyl)acetate (Example 15, 1.75 kg, 3.27 mol, 1 eq) was slurried in toluene (15.2 kg, 10 mL/g) and warmed to 50° C. A 10% aq. solution of $K_2CO_3$ (1.75 kg $K_2CO_3$ dissolved in 17.5 L purified water, 10 mL/g) was charged. The mixture was stirred vigorously at 50° C. for 30 minutes. The two solution phases were separated at 50° C. The organic phase was washed with purified water (1.75 kg, 1 mL/g) at 50° C. The phases were separated at 50° C. and the toluene volume reduced to 3 mL/g (5.5 L) by distillation. Crystallization was performed by reducing the temperature to 62° C. and then cooling to 40° C. over 40 mins. The batch was held at 40° C. for 30 mins and then seeded using (R)-2-[3-(diisopropylamino)-1-phenylpropyl]-4-(hydroxymethyl)phenol (0.01 kg, prepared previously using a similar method on a smaller scale). The batch was agitated for a further 1 hour at 40° C. and then cooled to 20° C. over 3.5 hours. The batch was granulated at 20° C. for 10 hours. The slurry was then cooled to 2° C. over 1 hour and granulated at 2° C. for 1 hour (see temperature profile below). The suspension was filtered and the cake washed with cold toluene (1.5 kg, 1 mL/g). The damp product (0.933 kg, dry estimated by % LOD analysis) was a white crystalline solid.

A toluene re-slurry was then performed. Toluene (2.42 kg, 2.6 mL/g (based on dry estimate)) cooled to 3° C. and damp product was charged and agitated at 3° C. for 15 mins. The suspension was filtered and the cake washed with cold toluene (1.6 kg, 1.5 mL/g (based on dry estimate)). The damp product was dried in vacuo at 45° C. to yield (R)-2-[3-(diisopropylamino)-1-phenylpropyl]-4-(hydroxymethyl)phenol (0.74 kg, 2.17 mol) in 66.7% yield as a white crystalline solid. HPLC indicates >99.6% purity, and chiral HPLC indicates >99% ee.

EXAMPLE 17

Preparation of (R)-(+)-isobutyric acid 2-[3-(diisopropylamino)-1-phenylpropyl]-4-(hydroxymethyl)phenyl ester

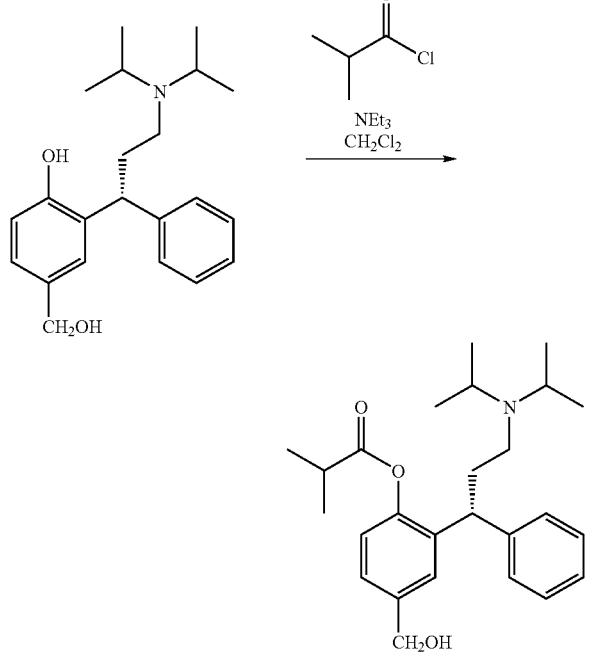

The title compound is prepared from the compound of Example 16 using the method of U.S. Pat. No. 6,858,650 (see section 5, column 16). Alternatively, this reaction can be performed without the addition of an external acid-intercepting base (U.S. Pat. No. 6,858,650, column 10, lines 32-40).

EXAMPLE 18

Preparation of (R)-(+)-isobutyric acid 2-[3-(diisopropylamino)-1-phenylpropyl]-4-(hydroxymethyl)phenyl ester hydrogen fumarate

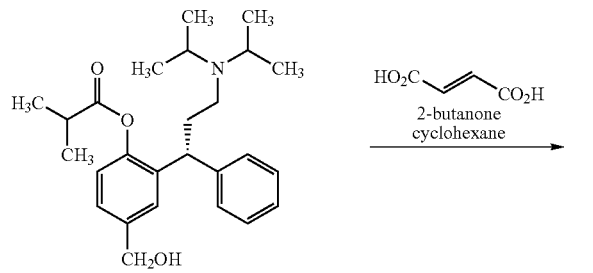

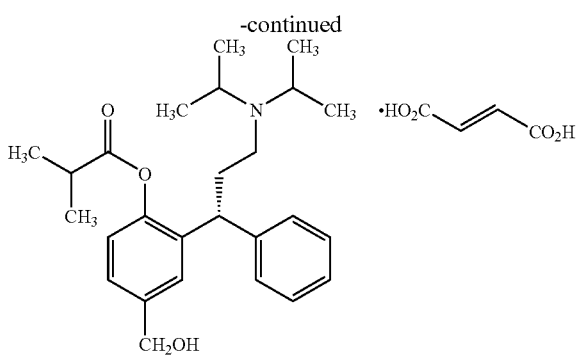

The title compound is prepared from the compound of Example 17 using the method of U.S. Pat. No. 6,858,650 (section 6, column 16).

EXAMPLE 19

Synthesis of [2-(4-Methylpiperazin-1-yl)-4-phenyl-2H-chroman-6-yl]-methanol

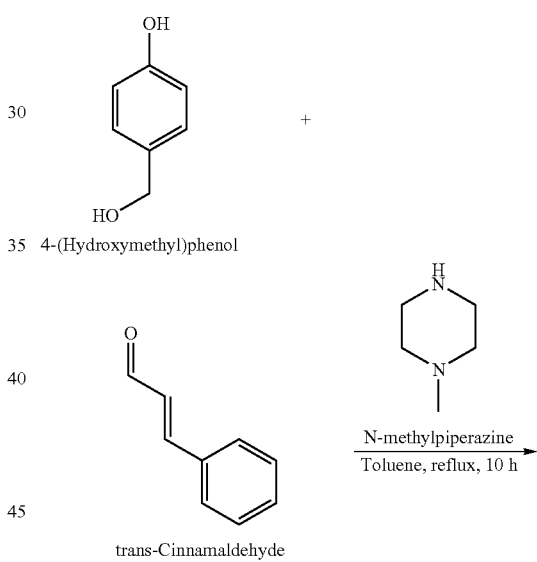

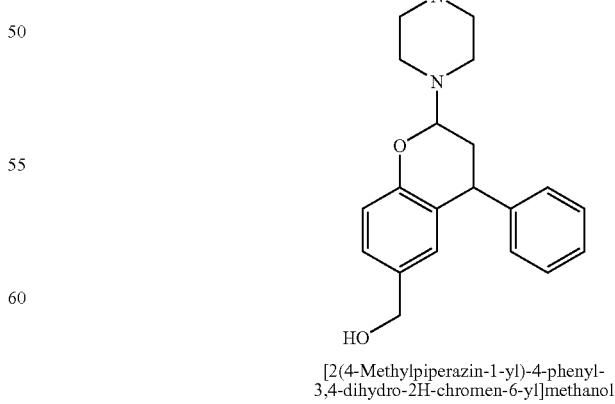

[2(4-Methylpiperazin-1-yl)-4-phenyl-3,4-dihydro-2H-chromen-6-yl]methanol trans-Cinnamaldehyde (66.5 g, 0.66 mol, 1.25 eq) was diluted with toluene (100 mL, 2 mL/g based on 4-(hydroxymethyl)phenol), and was washed twice with a saturated solution of sodium hydrogen carbonate (2×100 mL) and once with water (100 mL). This toluene solution of cinnamaldehyde was then added over 2 hours to a mixture of 4-(hydroxymethyl)phenol (50 g, 0.40 mol, 1 eq) and N-methylpiperazine (113 mL, 1.0 mol, 2.5 eq) in toluene (350 mL, 7 mL/g) heated to reflux under Dean-Stark conditions. Once the addition was complete the reaction mixture continued to be heated at reflux under Dean-Stark conditions for 10 h. The mixture was then cooled to room temperature and a sample was evaporated to dryness under reduced pressure for analytical purposes. The dark oil contains crude [2-(4-methylpiperazin-1-yl)-4-phenyl-2H-chroman-6-yl]methanol (mixture of diastereoisomers) and impurities.

EI-GC-MS (Agilent), column: ZB-5HT, Temperature program: 50° C. (0.5 min), 20° C./min to 320° C. (2 min) obtained: RT=24.4 min, MW: 338.

$^1$H NMR (DMSO) (crude mixture) 300 mHz δ (ppm): 7.40-7.00 (28H, m); 6.89 (1H, d, J=2.0 Hz); 6.81 (1H, d, J=8.3 Hz); 6.75 (1H, d, J=8.2 Hz); 6.54 (1H, d, J=1.0 Hz); 4.87 (1H, d, J=10.2 Hz); 4.45 (1H, d, J=10.0 Hz); 4.40-4.20 (3H, m); 4.36 (2H, s); 4.23 (1.8H, s); 2.86 (4H, m); 2.80-2.50 (14H, m); 2.50-2.00 (50H, m) including 2.31 (s); 2.17 (s); 2.14 (s); 2.11 (s).

The synthesis of fesoterodine hydrogen fumarate according to the methods of Examples 13-18 is shown in Scheme 3 below.

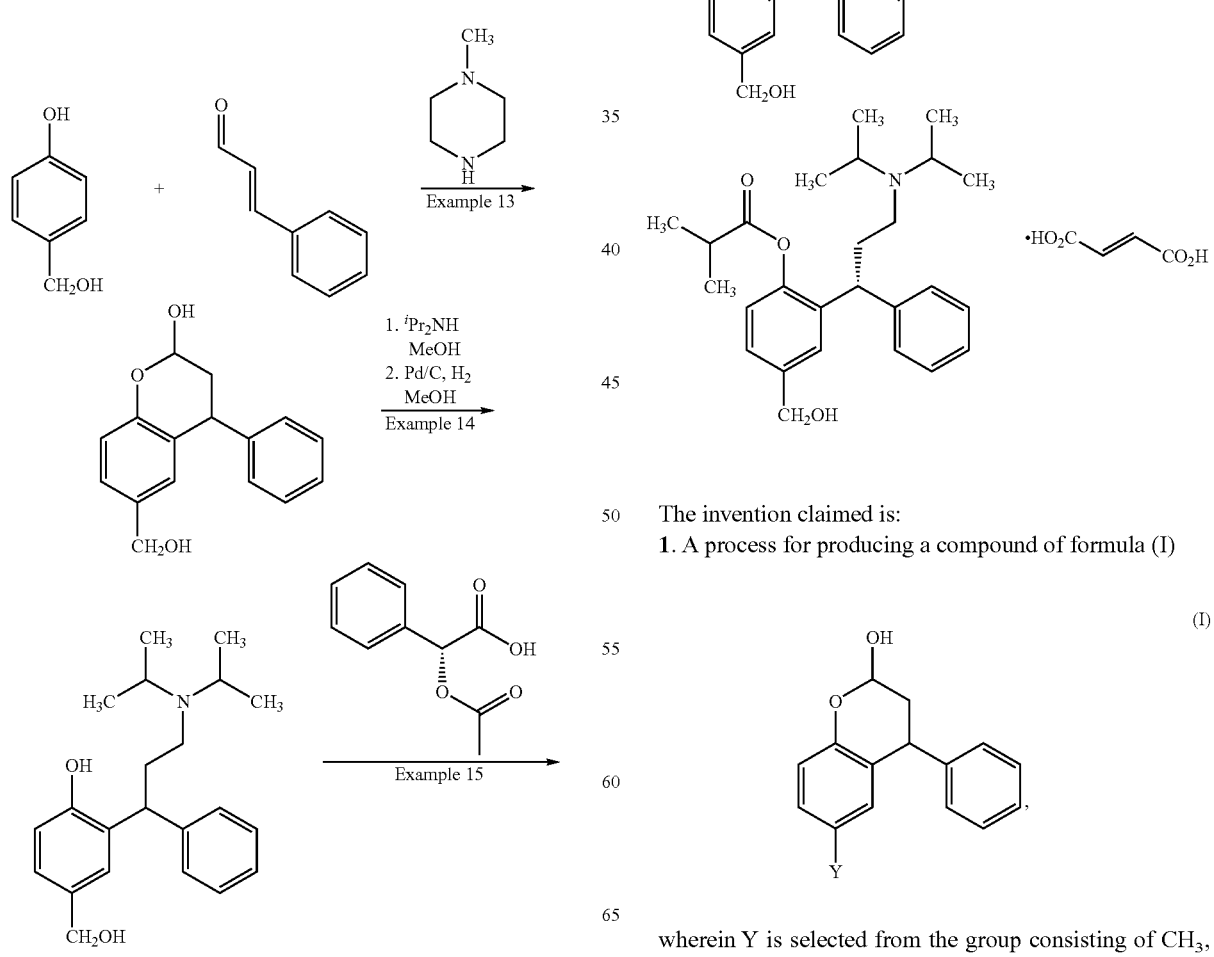

The invention claimed is:

1. A process for producing a compound of formula (I)

wherein Y is selected from the group consisting of CH$_3$, and CH$_2$OH, comprising the steps of:

(i) reacting a compound of formula (II),

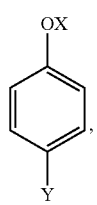

(II)

wherein OX represents hydroxy or $O^-M^+$, in which $M^+$ is a cation selected from $Li^+$, $Na^+$ and $K^+$, and
Y is as defined above;
with trans-cinnamaldehyde (III),

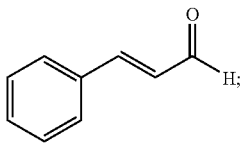

(III)

in the presence of a secondary amine compound; then
(ii) treating the product of the preceding step with acid to afford the compound of formula (I).

2. The process of claim 1, wherein OX represents hydroxy.

3. The process of claim 1, wherein the secondary amine compound is achiral.

4. The process of claim 1, wherein the secondary amine compound contains two secondary amine groups.

5. The process of claim 1, wherein the secondary amine compound is piperazine.

6. The process of claim 4, wherein 0.5-1.25 mole equivalents of the secondary amine compound are used in step (i).

7. The process of claim 1, wherein the secondary amine compound contains one secondary amine group.

8. The process of claim 1, wherein the secondary amine compound is morpholine, dibutylamine, dibenzylamine, 1,1,3,3-tetramethylguanidine, diethylamine, diisopropylamine, piperidine or an N—($C_{1-6}$ alkyl)piperazine.

9. The process of claim 8, wherein the secondary amine compound is N-methylpiperazine.

10. The process of claim 7, wherein 1-5 mole equivalents of the secondary amine compound are used in step (i).

11. The process of claim 1, wherein the acid used in step (ii) is aqueous hydrochloric acid.

12. The process of claim 1, wherein the reaction of step (i) is carried out in an organic solvent selected from toluene, xylene, N-butyl acetate, t-amyl alcohol, dioxane and dibutyl ether.

13. The process of claim 12, wherein the solvent is toluene.

14. The process of claim 1, wherein the reaction of step (i) is carried out at a temperature in the range 80° C. to the reflux temperature of the solvent.

15. The process of claim 1, wherein the reaction of step (i) is carried out under conditions that remove water from the reaction system.

16. The process of claim 1, wherein the reaction of step (i) is carried out at or around ambient pressure.

17. A process for producing a compound of formula (IV),

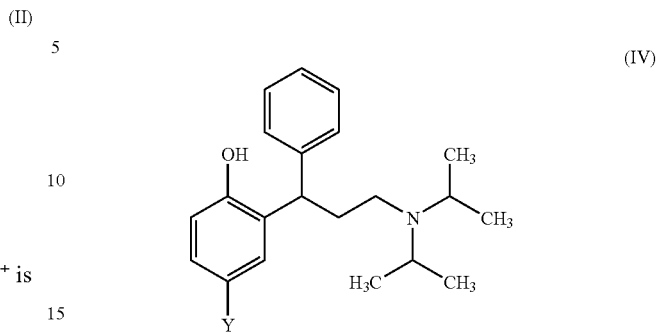

(IV)

wherein Y is selected from the group consisting of $CH_3$, and $CH_2OH$, or a salt thereof, comprising:

(a) producing a compound of formula (I):

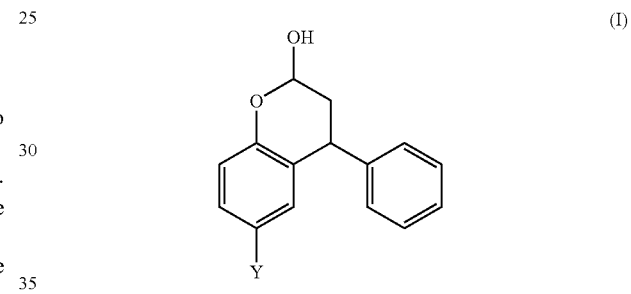

(I)

wherein Y is selected from the group consisting of $CH_3$ and $CH_2OH$ using the process claimed in any one of the preceding claims; then (b) reductively aminating the compound of formula (I) with diisopropylamine;

(c) and where desired converting the resulting compound into a salt.

18. The process of claim 17, wherein Y is $CH_3$, the compound of formula (IV) is treated with L-tartaric acid in step (c), and tolterodine L-tartrate is produced.

19. A process for producing fesoterodine,

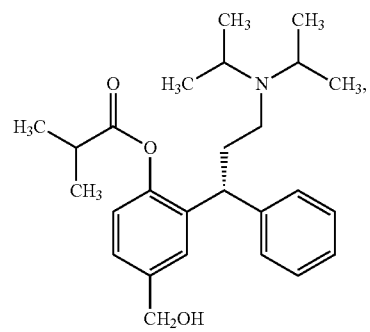

or a pharmaceutically acceptable salt thereof, which comprises:

(a) producing a compound of formula (IV),

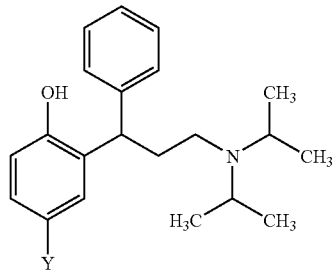

(IV)

in which Y is CH₂OH, using the process of claim 17; then (b) resolving the product of step (a) to obtain the (R)-enantiomer;

(c) acylating the phenolic hydroxy group of the product of step (b) to produce the corresponding isobutyric acid ester;

(d) and, where desired or necessary, converting the resulting compound into a pharmaceutically acceptable salt.

20. The process of claim 19, wherein the secondary amine compound used to produce the compound of formula I is N-methylpiperazine.

21. A compound of formula (V),

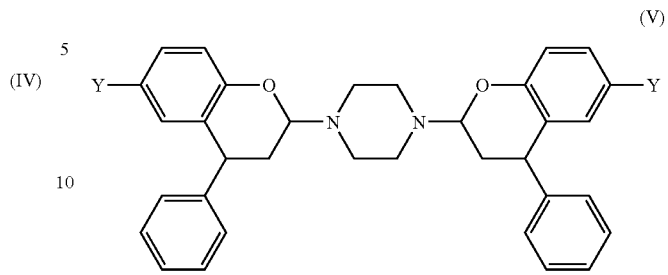

(V)

or a salt thereof, wherein Y is selected from the group consisting of $CH_3$, and $CH_2OH$.

22. A compound of formula (VI),

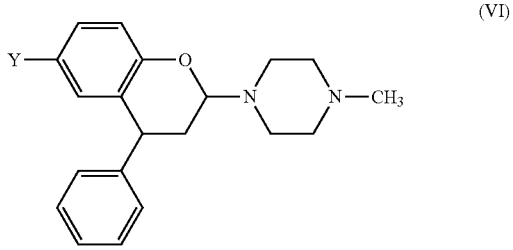

(VI)

or a salt thereof, wherein Y is selected from the group consisting of $CH_3$, and $CH_2OH$.

* * * * *